United States Patent [19]

Leonard et al.

[11] Patent Number: 5,039,660

[45] Date of Patent: Aug. 13, 1991

[54] PARTIALLY FUSED PEPTIDE PELLET

[75] Inventors: Robert J. Leonard, Lynnfield, Mass.; S. Mitchell Harman, Ellicott City, Md.

[73] Assignee: Endocon, Inc., South Walpole, Mass.

[21] Appl. No.: 163,328

[22] Filed: Mar. 2, 1988

[51] Int. Cl.$^5$ ............................................ C07K 17/08
[52] U.S. Cl. .................................... 514/8; 514/12; 514/14; 514/15; 514/16; 514/17; 514/18; 514/19; 514/800
[58] Field of Search .................. 514/8, 12, 14, 15, 16, 514/17, 18, 19, 800

[56] References Cited

U.S. PATENT DOCUMENTS

| | | | |
|---|---|---|---|
| 4,164,560 | 8/1979 | Folkman et al. | 424/427 |
| 4,591,496 | 5/1986 | Cohen et al. | 424/78 |
| 4,667,014 | 5/1987 | Nestor, Jr. et al. | 514/800 |
| 4,801,577 | 1/1989 | Nestor, Jr. et al. | 514/800 |

Primary Examiner—Lester L. Lee
Attorney, Agent, or Firm—Wolf, Greenfield & Sacks

[57] ABSTRACT

A bioerodible pellet capable of administering an even and continuous dose of a peptide over a period of up to a year, when subcutaneously implanted, is provided. The bioerodible implant is a partially-fused pellet, which pellet has a peptide drug homogeneously-bound in a matrix of a melted and recrystallized, nonpolymer carrier. Preferably, the nonpolymer carrier is a steroid and in particular is cholesterol or a cholesterol derivative. In one embodiment, the peptide drug is growth hormone-releasing hormone. A method for making the bioerodible pellet also is provided.

13 Claims, 4 Drawing Sheets

PARTIALLY FUSED PEPTIDE PELLET

This invention relates generally to drug delivery systems and particularly to a bioerodible pellet capable of delivering a peptide when implanted subcutaneously.

BACKGROUND OF THE INVENTION

Since the elucidation of the clinical significance of certain naturally-occurring peptides and the development of various techniques for their synthesis, it has become clear that these substances will be clinically practical only if a convenient method for delivering them in controlled doses can be provided. Because peptides are destroyed in the digestive tract when taken orally, they must be administered parenterally. Furthermore, therapies involving bioactive peptides often demand injections at regular intervals for extended periods of time. In view of these limitations, certain controlled release drug delivery systems for providing continuous parenteral dosing of peptides have been sought. While continuous infusion systems such as pumps have been used, they are cumbersome, expensive and not completely practical.

Efforts have been made to employ existing drug delivery systems based on biodegradable polymers as subcutaneous implants for the controlled release of peptides. Current polymer-based systems are typically combined with a drug in one of the following ways: (1) Diffusion systems in which a reservoir of drug is contained in a polymer capsule and drug delivery is by the slow diffusion of the drug through the interstices of the polymer capsule wall; (2) matrix erosional systems (monolithic systems) in which a drug is evenly distributed in a polymer matrix and is released as the polymer breaks down in biological fluid; and (3) diffusion/erosion systems in which drug release occurs as a result of diffusion of the drug through the polymer matrix and release of the drug as the surface of the device continually erodes.

Numerous difficulties associated with achieving the release of peptides from polymer systems have been encountered in the laboratory. While these difficulties are acknowledged, they are not well understood and may be the result of several physiochemical events acting in concert. For example, certain peptides tend to aggregate—perhaps due to ionization—under conditions where high concentrations of the peptides come into contact with phosphate buffered physiologic saline solution used to simulate the extracellular environment the implant will be in. This effect has proven to be a significant obstacle in the development of diffusion type polymer devices. So-called aggregation is particularly likely in the case of selectively porous polymer capsules. These capsules present a synthetic diffusion layer having pores of specific size and frequency whereby biological fluids first seep into the capsule, dissolve the encapsulated drug and then carry the drug back out to a saturated reservoir (formed by the normal reaction of subcutaneous fibrous tissue to the presence of the capsule) surrounding the implant. In such systems, depending on the net charge of the molecule and the size of the pores (dictated by the size of the molecule), enough biological fluid will enter the capsule to reach a critical point at which aggregation takes place and the drug assumes the consistency of a thick gel that resists diffusion from the capsule.

Alternatively, there are those diffusional capsules which rely on the seeping out of drug through the interstices of the polymer structure. With the exception of a few peptides of comparatively low molecular weights (such as luteinizing hormone-releasing hormone), peptide molecules of physiologic interest have been shown to be too large to escape these capsules.

Difficulties with polymer-based delivery systems also may arise from a reaction between the peptide and the hydrolized by product of the polymer or some additive used as a wetting agent, or a confluence of such circumstances. Conversely, the known monolithic polymer systems exhibit a bulk erosion, thus releasing too much (or all) of the drug and cannot be relied upon to provide appropriate release kinetics over long periods of time.

Nonpolymer-based devices have also been used as subcutaneous implants for delivering a drug. Initially, pellets formed by compressing mixtures of a drug and an excipient were attempted. Such pellets, however, tended to disintegrate after a short time and thus exhibited an undesirable burst effect of the active ingredient and short duration of action. Later, pellets formed by "fusing", rather than compressing, mixtures of a drug and an excipient were attempted. In particular, fused pellets for the controlled release of steroid hormones were made by melting a mixture of cholesterol and a steroidal hormone under strictly controlled conditions. The completely melted ixture would be allowed to cool and recrystallize. It has been determined that such a fused pellet, if properly manufactured, releases steroidal hormones in a relatively even and continuous manner over a period of a year or more. It is believed that diffusion is minimized in such pellets, if existent at all. Rather, the uniform release rate is due to the slow surface erosion of the pellet, the active ingredient being evenly distributed across the surface of the pellet and uniformly throughout its volume.

Fused implants have never been used as a system for delivering peptides. In the totally-fused pellet, the hard, final matrix is arrived at by the creation of a complete melt that recrystallizes during cooling. This is not possible with a peptide molecule which, if melted, may fragment and lose its bioactivity.

The present invention provides a simple, inexpensive, nonpolymer, erodible pellet for subcutaneous implantation providing continuous parenteral release of peptides. The present invention also provides a method and apparatus for the preparation of such bioerodible pellets.

SUMMARY OF THE INVENTION

A bioerodible pellet capable of administering an even and continuous dose cf a peptide over a period of up to a year when subcutaneously implanted is provided. The bioerodible implant is a partially fused pellet, which pellet has a peptide drug homogenously bound in a matrix of a melted and recrystallized, nonpolymer carrier. The carrier is bioerodable, highly crystalline and lipophilic.

The partially fused pellet is made by forming a homogenous mixture of a bioerodible nonpolymer carrier and a peptide, the carrier having a lower melting temperature than the peptide. The mixture is then heated to a temperature to cause the carrier to melt, but not so high as to cause the peptide to melt or degrade. Thus a partially-melted solution is formed, substantially all of the carrier being melted and substantially all of the peptide not melted. Then, the partially-melted solution is allowed to cool into a hardened pellet.

Most preferably the carrier is a sterol (i.e., cholesterol or a cholesterol derivative or an ester thereof). Non-sterol carriers having properties similar to the foregoing sterols when melted, recrystallized and implanted in the body may be substituted. The peptide drug may be any bioactive peptide, and according to one preferred embodiment, is growth hormone-releasing hormone (GHRH). The peptide and carrier must be selected such that the peptide will not melt, degrade or otherwise lose its bioactivity when in a suspension of the melted carrier at about the melting temperature of the carrier for a short duration.

The pellet may be formed in a chamber having a fluorocarbon surface to avoid sticking. The homogeneous mixture of the carrier and peptide may be added to the chamber as a paste. In particular, an alcohol paste may be formed from the mixture and a measured amount of the paste may be added to the chamber. Then the alcohol is evaporated out of the mixture leaving the carrier and the peptide in the chamber. Preferably the homogeneous mixture is compressed in the chamber prior to forming the partial melt. Likewise, it is preferable to maintain the partially-melted solution under pressure in the chamber as the carrier recrystallizes and the hardened pellet forms.

According to a preferred method for forming a pellet, the homogeneous mixture of carrier and peptide is introduced into a fluorocarbon tube having a lumen of specific diameter. Then, one end of the tube is fitted with a plug, the plug sized to fit totally and sealingly within a portion of the tube. Next the tube is placed such that the plugged end abuts a solid surface. Then a compression pin is introduced into the bore at the opposite end of the tube, and the homogeneous mixture is compressed by applying pressure via the compression pin. The tube is then introduced into an oven and left in the oven until the partial melt is formed. Then the tubing is removed from the oven. Again, the plugged end of the tubing is placed to abut a solid surface and pressure is applied to the partially-melted solution via the compression pin while said partially-melted solution cools into a hardened pellet. Then the plug and hardened pellet may be expelled from the tube.

The hardened pellet may be used in treating various health conditions that require an even and continuous dose of a peptide drug, including endocrinologically-mediated disorders, disorders of aging and certain cancers. The pellet is implanted subdermally. The pellet undergoes surface erosion releasing the peptide continuously for an extended period of time. Because the means of drug release is based on pure surface erosion, the pellet does not exhibit a significant burst effect and does not result in the aggregation of peptide once implanted.

In addition to providing an implantable pellet capable of sustained release of a peptide over an extended period of time and a method for making such a pellet, an apparatus for making such a pellet is provided.

DETAILED DESCRIPTION OF THE DRAWINGS

Figure 1:
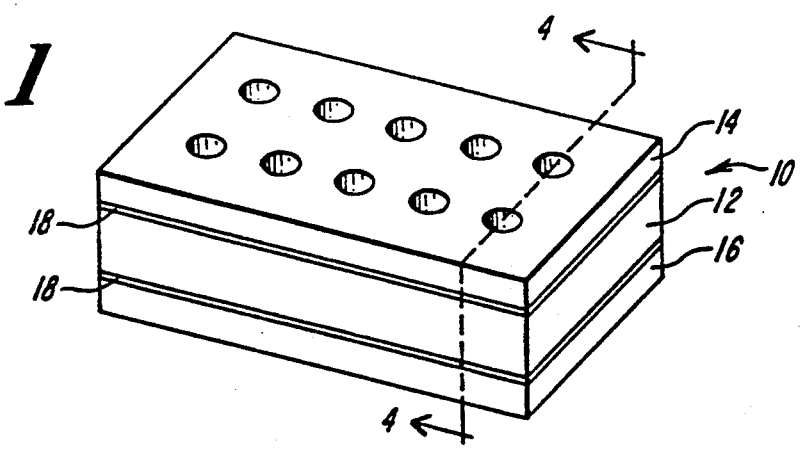
FIG. 1 is a side elevated view of an apparatus according to the invention.
Figure 2:
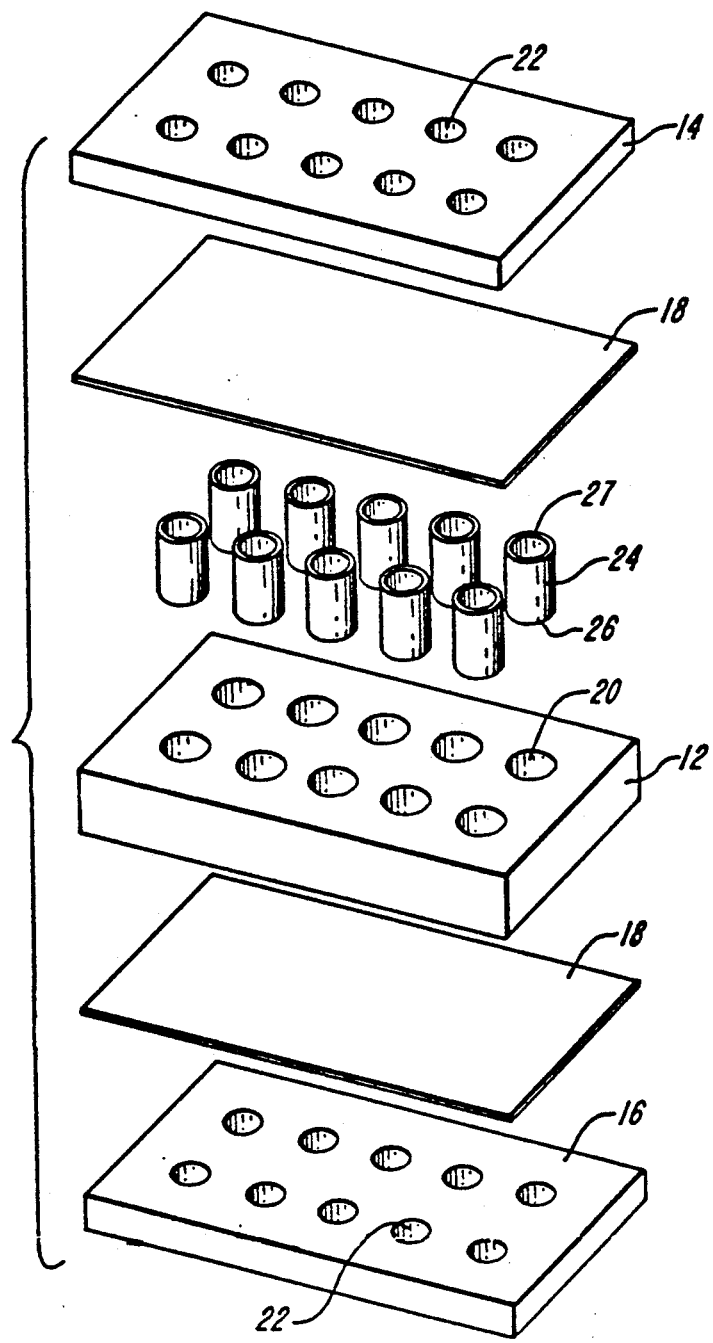
FIG. 2 is an exploded view of FIG. 1.
Figure 3:
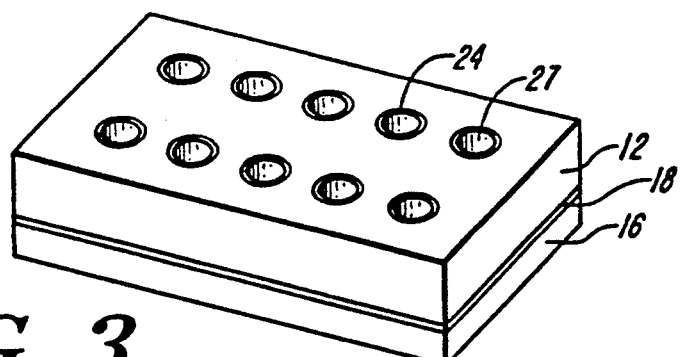
FIG. 3 shows the elements of FIG. 2 assembled for the paste delivery step.
Figure 4:
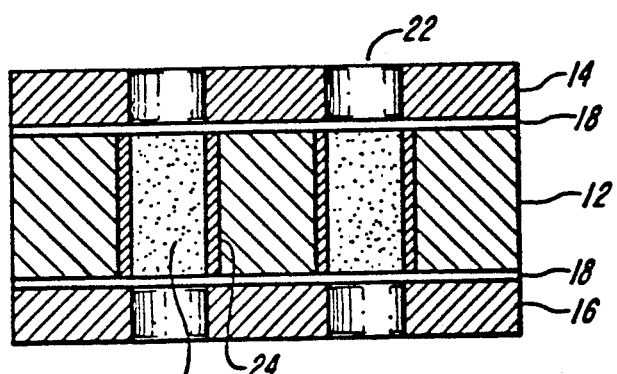
FIG. 4 is a cross sectional view of FIG. 1 along line 4—4 and illustrates the paste-drying step.

According to the invention, a peptide drug is homogeneously distributed and captured in a matrix of a melted and recrystallized nonpolymer carrier. A carrier having a lower melting point than the peptide is selected so that when a homogeneous mixture of the carrier and peptide is heated, a partial melt may be formed with substantially all of the carrier melting and substantially all of the peptide drug not melting. The partial melt then is allowed to cool, with the carrier recrystallizing to form the hardened pellet and capture the peptide drug.

The nonpolymer carriers according to the invention are lipophilic. They also are bioerodible and, therefore, do not have to be removed surgically when the drug has been depleted as is the case with many of the prior art devices. Preferably, the nonpolymer carrier is metabolized or excreted as the pellet erodes. Most preferably, the nonpolymer carrier is one that occurs naturally in the human body.

The nonpolymer carriers according to the invention are of relatively small molecular weight as compared to the macromolecular polymer carriers of the prior art. For example, the molecular weight of a preferred carrier, cholesterol acetate, is approximately 428 daltons, whereas the molecular weight of the typical polymer carrier of the prior art is believed to be on the order of $10^3$–$10^6$ daltons, depending on the degree of polymerization. The nonpolymer carriers according to the invention also are typically smaller than the peptide drug that is captured in the matrix of the recrystallized carrier. Nearly all peptide drugs have between about 8 and 60 amino acids and range from approximately 1,000 to 7,500 daltons in molecular weight (although one unusually small peptide drug, peptide-T, has only three amino acids and, therefore, has approximately the same molecular weight as a preferred carrier, cholesterol acetate.) Preferably, the nonpolymer carriers also are highly crystalline, especially as compared with the typical polymer carriers of the prior art. The foregoing properties contribute to the favorable characteristics of the formed pellet.

One embodiment of the invention is a partially fused pellet consisting essentially of pure cholesterol acetate as the carrier and growth hormone releasing hormone, which has approximately 40 amino acids, as the bioactive peptide drug. Powdered GHRH is mixed with powdered cholesterol acetate. The mixture is heated until the cholesterol acetate, but not the GHRH, melts.

The partial melt is then allowed to cool, with the cholesterol acetate recrystallizing to form a pellet.

Recrystallization of cholesterol has been observed to follow a "ferning" pattern, beginning at the center of the melt and branching outwardly in all directions with increasing geometric complexity until all of the melted material has hardened. The GHRH is thus bound in a complex skeletal network of the recrystallized carrier.

The GHRH/cholesterol acetate pellet erodes slowly in vitro due to the lipophilicity and high crystallinity of the carrier. The rate of release of GHRH from the pellet is consistent with pure surface erosion. The relatively larger size of the GHRH, as compared to the cholesterol acetate, makes escape of the GHRH through the crystal matrix of the cholesterol acetate unlikely, if not impossible. There also is no aggregation of GHRH within the pellet, at least in part because the lipophilic and highly crystalline pellet resists absorption of biological fluids. (GHRH has been shown to aggregate in polymer diffusion systems.)

The GHRH/cholesterol acetate pellet has other favorable properties. Because the carrier and the drug order are both naturally occurring substances, the time and expense associated with determining the potential toxicity of a synthetic substance are eliminated. Likewise, the costs associated with synthesizing a high or complex polymer carrier are avoided. Further, the disparity in molecular weight between the GHRH and the cholesterol acetate allows a superb surface ratio of active ingredient to carrier as well as great flexibility for surface area adjustment by regulation of both pellet size and the ratio of active ingredient to carrier.

Preferably the nonpolymer carrier is cholesterol or a cholesterol derivative including, but not limited to, cholesterol acetate and cholesterol chloride. Other preferred nonpolymer carriers include sterols other than cholesterol, steroids, steroid derivatives and analogues and other bioerodable compounds having lipohilic and crystalline properties, size and a melting temperature similar to cholesterol and cholesterol derivatives. Other carriers that may be substituted include certain fatty acids or neutral fats such as mono-, di- or triglycerides (or a combination of two or more of such lipid molecules) that have erosion properties and release kinetics similar to the foregoing sterols when combined with a peptide, melted, recrystallized and implanted in the body. The carrier must have a melting temperature such that it is a solid at body temperature (above about 40° C.) and such that the peptide of choice will not melt, degrade or otherwise lose its bioactivity when in a suspension of the melted carrier at about the melting temperature of the carrier for a short duration.

The peptide may be any bioactive peptide, naturally occurring or synthetic. Included are the classes of peptides known as neuropeptides and regulatory peptides. Specific examples of such factors include, but by no means are limited to, growth hormone and growth hormone-releasing hormone, gonadotropin-releasing hormone, and its agonist and antagonist analogues, somatostatin and its analogues, gonadotropins such as luteinizing hormone and follicle stimulating hormone, peptide-T, thyrocalcitonin, parathyroid hormone, glucagon, vasopressin, oxytocin, alpha and beta melanocyte-stimulating hormones, peptide molecules which stimulate erythrocyte, leucocyte and immunocyte growth and function such as colony stimulating factors (CFS 1 and 2), erythropoietin and lymphokines (including interleukin I and II), angiotensin I and II, bradykinin, kallidin, adrenocorticotropic hormone, thyroid stimulating hormone, insulin, glucagon and the numerous analogues and congeners of the foregoing peptides. It should be understood that the term peptide is intended to include small proteins, and particularly those molecules having on the order of about 100 amino acids or less.

Accurate dispensing of the starting materials may be achieved by forming a paste made from a powdered mixture of the starting materials and a liquid such as ethyl alcohol, which alcohol may be dried out of the starting materials after dispensing, utilizing, for example, a standard vacuum oven. By forming a paste, the material can be dispensed accurately from a standard, automated device such as a micropipetter. The paste may be manufactured to have the flow characteristics of ordinary toothpaste.

The formation of the paste clearly overcomes problems of the prior art. Where drugs such as peptides are concerned, anything but a precise dosage could either be ineffective or harmful to the user. The standard pharmaceutical-dispensing machinery for powders does not dispense the very small quantities of powder required for the individual pellets of the invention with sufficient accuracy. This is especially true when the active ingredient comprises 50% or more of the total pellet volume. Therefore, according to the prior art, the materials must be measured and carefully allocated separately for each pellet. By forming a paste, the precise relative amounts of drug and carrier are maintained homogeneously throughout the paste and individual manual measurements are thus obviated.

The liquid agents used to formulate the paste may be ethyl alcohol or any volatile organic solvent which can be evaporated completely prior to forming the partial melt and which by combining with the starting materials yields suitable flow characteristics. The liquid agent should be of a nature that promotes quick drying of the paste once the paste is dispensed. The liquid agent, of course, should not be of a nature which affects the activity of the active agent in the pellet.

The drawings illustrate a preferred method and apparatus for forming the peptide pellet of the invention. Since the mixture of the peptide and carrier will be allocated as a paste, an evaporation assembly 10 for drying the paste is provided (FIGS. 1–4). The evaporation assembly 10 includes a rectangular holding block 12 sandwiched in face to face relation between a top plate 14 and a bottom plate 16 A filter sheet 18 lays between the facing surfaces of the top plate 14 and the holding block 12. Likewise, a filter sheet 18 lays between the facing surfaces of bottom plate 16 and the holding block 12.

The holding block 12 is made of lucite and is 0.625 inches thick. Other materials, of course, may be substituted for lucite. A plurality of bores extends through the holding block 12. These block bores 20 are sized to matingly receive fluorocarbon tubes in which the peptide pellets will be formed. The block bores 20 have a diameter slightly greater than the outer diameter of the fluorocarbon tubes, or slightly greater than 0.135 inches so that the tubes will move freely in the block bores 20.

The top plate 14 and the bottom plate 16 also are made of lucite and are about 0.125 inches thick. A plurality of bores having a diameter of 0.095 inches extends through the top and bottom plates 14, 16. These plate bores 22 are positioned in the top and bottom plates 14, 16 such that they can be aligned to mate concentrically with the block bores 20 when the top and bottom plates 14, 16 are positioned to sandwich the holding block 12. Thus, the aligned plate and block bores 22, 20 will define passages extending completely, through the assembled evaporation chamber.

The fluorocarbon tubes 24 will be placed in the block bores 12, held in place by the top and bottom plates 14, 16. The fluorocarbon tubes are straight cylinders having an inner diameter of 0.095 inches and an outer diameter of 0.135 inches. They are cut to a length of 0.625 inches. This length is the same as the length of the block bores 12 such that the ends of the fluorocarbon tubes 24 lie flush with the plate facing surfaces of the holding block 12. Fluorocarbon tubing sold under the name of Teflon-TFE, Norton Chemplast, Inc., of Wayne, N.J. has been used successfully. It should be understood that only the inner surface of the tubing need be a non-stick surface and that the tube may be made from nearly any material that is at least semi rigid so long as the material will accept a fluorocarbon coating and will not melt or soften under the conditions applied in forming the melt.

The diameter of the plate bores 22 is smaller than the diameter of the block bores 20. When the top and bottom plates 14, 16 are attached to the holding block 12 with the block bores 20 and plate bores 22 aligned, the ends 26 of the fluorocarbon tubes 24 will abut the facing surfaces of the top and bottom plates 14, 16 about the periphery of plate bores 22, and the top and bottom plates 14, 16 will hold the fluorocarbon tubes 24 within the block bores 20. The diameter of the plate bores 22 is equal to the inner diameter of the fluorocarbon tubes such that a passage of uniform diameter defined by the plate bores 20, 22 and lumen of the fluorocarbon tubing extends through the assembled device.

The operation of the evaporation assembly 10 is as follows. A filter sheet is placed between the facing surfaces of the bottom plate 16 and the holding block 12. Preferably the filter sheet is a porous polymer filter having a pore size of 10 microns. Such a filter is obtainable under the trade name Gelman Versapore, 10-micron, sold by Gelman Sciences, Inc. of Ann Arbor, Mich. The bottom plate 16 then is attached to the holding block 12 such that the plate bores 22 and block bores 20 are aligned, with the filter sheet 18 separating the aligned bores. Then, the fluorocarbon tubes 24 are placed into the open end of the block bores 22, one end 26 of each fluorocarbon tube 24 lying flush with the surface of the holding block 12 facing the bottom plate 16 and the other end 27 of each fluorocarbon tube 24 lying flush with the surface of the holding block 12 facing the top plate 14. Next, an alcohol paste 28 containing the peptide and carrier is prepared. An aloquot of the paste 28 is dispensed into the top plate facing end 27 of each of the fluorocarbon tubes 24. After dispensing the alcohol paste 28, a filter sheet 18 is placed on the top plate-facing surface of the holding block 12 and the top plate 14 is attached to the holding block 12. The assembled device containing the fluorocarbon tubes is shown in cross section in FIG. 4. This evaporation assembly 10 containing the filled fluorocarbon tubes 24 then is placed in a vacuum oven to evaporate the alcohol completely out of the paste 28 (approximately 24 hours), leaving a homogeneous dry mixture 30 of the carrier and peptide.

It is preferable to compact the dry mixture of peptide and carrier to expel air from the dry mixture prior to forming the partial melt. To accomplish this, one end of the fluorocarbon tubes 24 is plugged with a plug 32 having a non-stick surface (such as Teflon TFE beading) and a compression pin is introduced into the opposite end of the fluorocarbon tubes 24 to densely pack the dry mixture 30 of the peptide and carrier against the plug 32.

Figure 5:
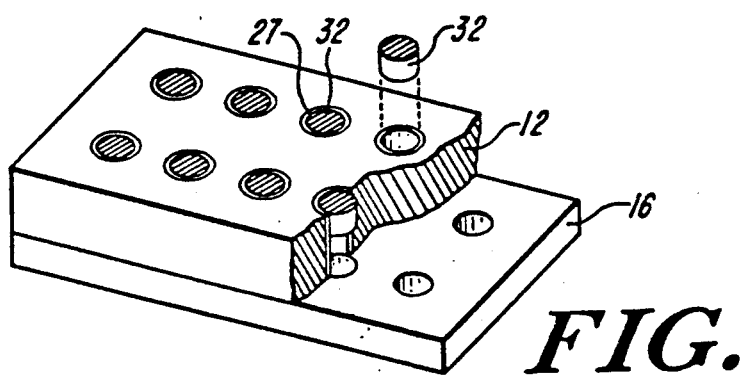
FIG. 5 shows the device of FIG. 4 with the top plate and top filter removed during the chamber-plugging step.
Figure 6:
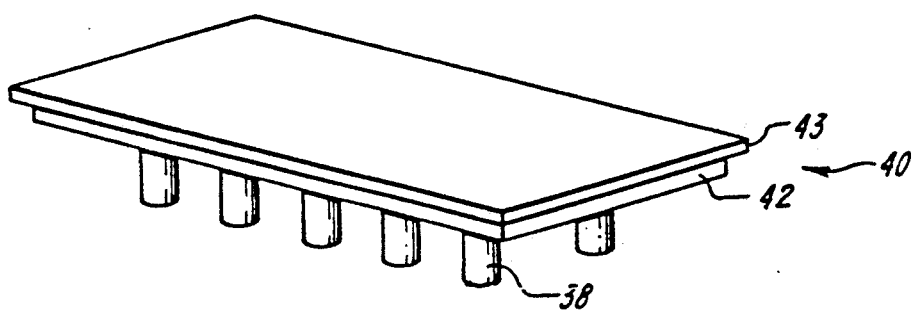
FIG. 6 illustrates the pin block used during the compression step.

Referring to FIG. 5, the top plate 14 and filter sheet 18 between the top plate 14 and holding block 12 are removed to expose the end 27 of the fluorocarbon tubes 24 facing the top plate 14. Then, a 3 millimeter long plug 32 of Teflon beading is friction-fit into the exposed end 27 of the fluorocarbon tubes 24. After plugging each of the fluorocarbon tubes 24, a solid top plate 36 then is attached in face-to-face relation to the holding block 12 to cover the plugged end of the flourocarbon tubes 24 and the holding block 12 is flipped over so that the solid plate 36 is on the bottom and the bottom plate 16 is on top. Next, the bottom plate 1 and the filter sheet 18 between the bottom plate 16 and the holding block 12 are removed, exposing the ends 26 of the fluorocarbon tubes 24 opposite the solid plate 36. Next, a plurality of pins 38 carried on a pin block 40 are fitted into the exposed ends of the fluorocarbon tubes 24. Referring to FIG. 6, the pin-block 40 preferably is a rectangular solid block carrying a plurality of pins 38. The pins 38 are spaced and aligned to mate with the fluorocarbon tubes 24. Each pin 38 is sized such that it friction-fits within the lumen of a fluorocarbon tube 24. In the embodiment described, stainless steel pins are carried on a Teflon block 42, friction fit into bores in the block, and the Teflon block is backed by a steel plate 43 which limits the travel of the pins.

Figure 7:
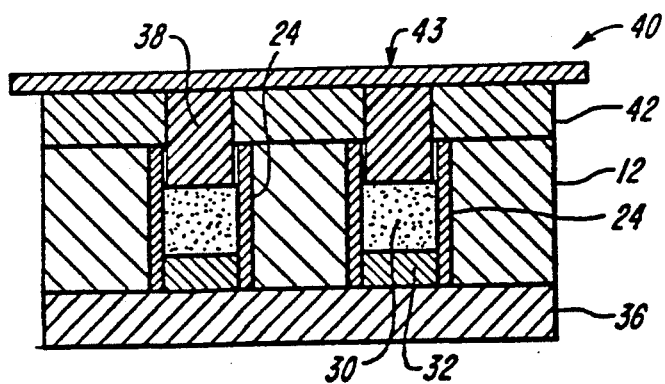
FIG. 7 is a cross sectional representation of an apparatus according to the invention during the compression step.

FIG. 7 illustrates in cross section the pin block 40 and solid plate 36 assembled onto the holding block 12 during the pre-melt compression step. The solid plate 36 and pin-block 40 sandwich the holding block 12. The plugs 32 of Teflon beading block one end of the fluorocarbon tubes 24. The plugs 32 abut the surface of the solid plate 36 facing the holding block 12. The compression pins 38 extend into the opposite end of the fluorocarbon tubes 24. Pressure is applied to the surface 44 of the pin block 40 opposite pins 38 to compress the dry mixture 30 of the carrier and peptide against the plugs 38. Preferably, on the order of about 2200 p.s.i. is applied.

Figure 8:
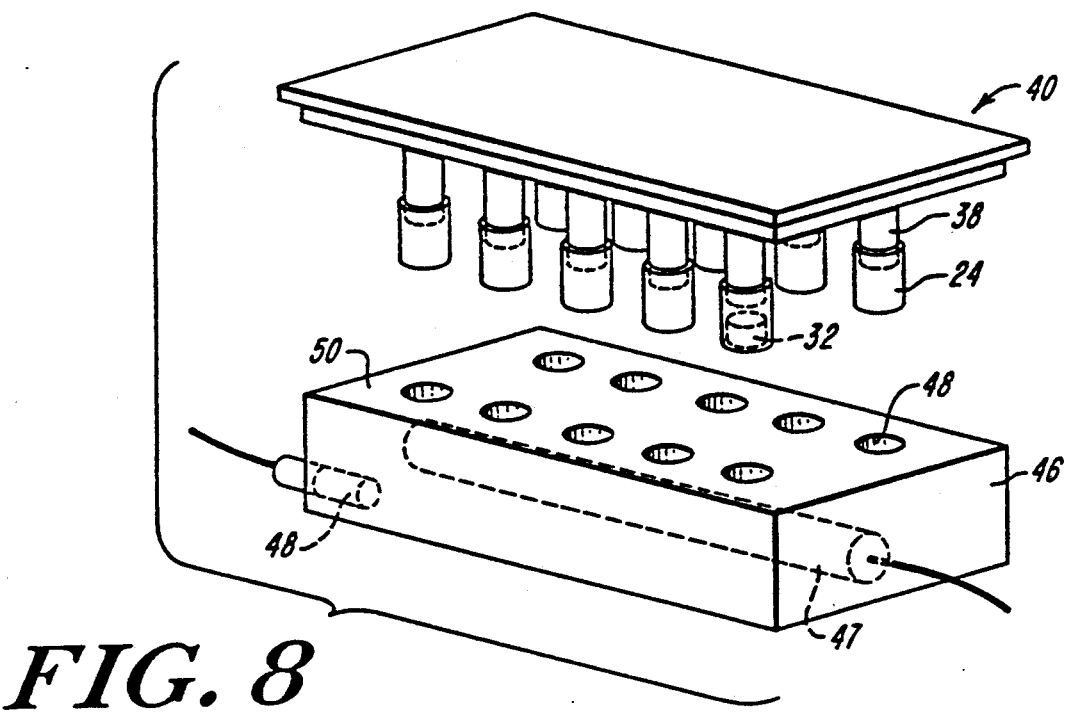
FIG. 8 shows the pin block carrying the chambers and suspended over the oven.
Figure 9:
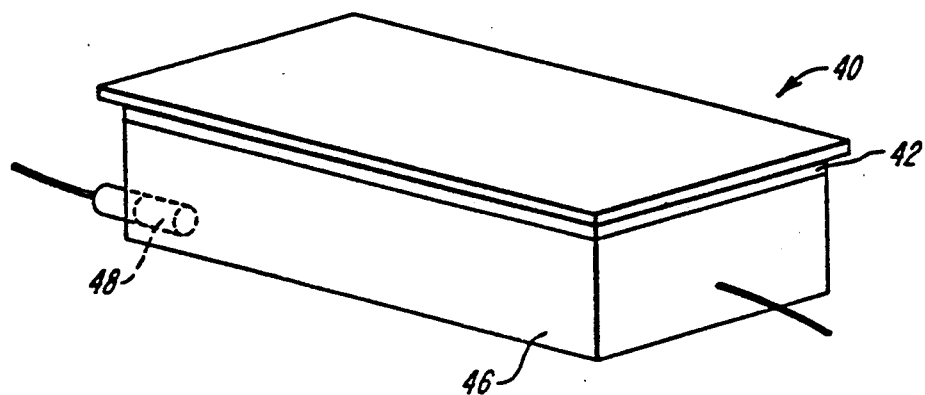
FIG. 9 illustrates an apparatus according to the invention during the melting step.

After the dry mixture 30 is compressed, the fluorocarbon tubes 24 containing the compressed dry mixture may be placed in an oven 46 to form the partial melt. Referring to FIG. 8, after the first compression step, the pinblock 40 is withdrawn from the holding block 12. Because of the friction fit between the pins 38 and the fluorocarbon tubes 24, the plugged fluorocarbon tubes are withdrawn from the holding block 12 along with the pins 38. The fluorocarbon tubes 24, carried on the pins 38, then are placed in the oven 46. Preferably the oven 46 is an aluminum block containing individual heating chambers 48 sized to receive and mate with the pins 38 and fluorocarbon tubes carried on the pins 38. The oven is heated by one or more resistance heating elements 47 under thermostatic control 48 and maintained at a temperature above the melting point of the carrier but below that which will melt or degrade the peptide. Thus, as shown in FIG. 9, each of the heating chambers 48 in the oven 46 receives an individual compression pin 38 carrying a fluorocarbon tube 24 containing the compressed dry mixture 30. The rectangular block 42 mates with the upwardly-facing surface 50 of the oven 46 to seal the individual fluorocarbon tubes 24 within their respective heating chambers 48. The compressed dry mixture 30 is left in the oven 46 until a partial melt is formed, that is, long enough until substantially all of the carrier melts but not so long as to melt any of the peptide.

When the partial melt is formed, the pin block 40 carrying the fluorocarbon tubes 24 is withdrawn from the oven 46 and immediately placed back into the compression chambers formed by the holding block 12 and solid plate 36. A slight compression (about 150 p.s.i ) is applied to the partial melt to ensure that as the partial melt cools and recrystallizes into a hardened pellet, the dimensions of the pellet and the surface characteristics of the pellet will not be affected by any fluctuation in the volume of the material as it cools. It is to be noted that the dose delivered by the hardened pellet depends, among other factors, on the surface area of the pellet. If the pellet is not subjected to a compressive force as it cools, then the surface of the pellet may have irregularities, as for example, in the form of valleys, bumps or a characteristic funnel-shaped impression at one end of the pellet. Such irregularities affect the structural integrity and the total surface area of the pellet and, correspondingly, the release kinetics of the pellet resulting from the erosion of the surface of the pellet. Thus, only by eliminating these irregularities can the surface area be accurately calculated and the release kinetics accurately predicted.

Using a plug with a non stick surface also helps to eliminate irregularities in the final product. As the material melts in the oven, the material expands. The non-stick plug is responsive to this expansion. That is, the plug moves in response to the expanding material. This movement prevents the expanding material from being forced between the facing surfaces of the plug and the tube and the pin and the tube. Likewise, when the tubes are removed from the oven, the material contracts and the plug is moved inwardly by the vacuum force created by this contraction. If the plug did not move, then air might be drawn into the pellet-forming chamber by the vacuum force prior to applying pressure in a second compression step. Likewise, if the plug did not move, the funnel shaped impression might begin to form prior to applying pressure in a second compression step. In fact, if the plug is sufficiently free to move responsively with the contracting material in the tube, it may not be necessary to have a second compression step, although a second compression step is preferable.

The plug and compression pin arrangement offers another important advantage by facilitating unidirectional compression. Compression causes pressure waves in the melted material. These waves affect the crystal lattice that forms as the material cools. If the compression is from both sides, the pellet may be weakened by fracture surfaces.

Preferably, the pellet is not quenched during the cooling step as it has been discovered that quenching may cause sudden contraction resulting in fractures in the hardened pellet. Once the pellet has hardened, it may be expelled from the fluorocarbon tube. The pellet then may be implanted subcutaneously and is capable of delivering a dose of peptide for up to a year.

EXAMPLE 1

Powdered cholesterol acetate obtained from Sigma Chemical Co. of St. Louis, Mo. growth hormone-releasing hormone obtained from Bissendorf Peptides of Gros Burgwedel, German Bundes Republik were combined in approximate proportions of 30% growth hormone-releasing hormone and 70% cholesterol acetate. The powder was dispensed into a fluorocarbon tube in an amount such that when dried, the remaining powder equaled approximately 2 millimeters in depth after the first compression phase. Approximately 20 grams of powder was added to the tube. The powder was added to the tube by placing the filter sheet described above at one end of the tube. A vacuum force then was applied across the filter sheet to suck the powder into the tube. The tube was plugged with a 3 millimeter piece of Teflon beading and the dry mixture was then compressed against the plug by hand, using a steel pin inserted into the end of the tube opposite the plug. The plugged end was held against a table top to prevent the plug from being expelled from the tube. The degree of compression corresponded to about 2200 p.s.i. for 3 seconds. Then the tube containing the compressed dry mixture was transferred on the pin to an oven preheated to 180° F. The tube was exposed to this environment for 30 seconds. The tube then was removed from the oven and compressed by hand at about 150 p.s.i. for about 6 seconds as the partially-melted material cooled and recrystallized to form a hardened pellet. The mixture was allowed to cool for an additional 3 minutes without any compression and, finally, the plugs and pellets were ejected from the Teflon tubes.

The results were hard, white pellets that did not crumble or show signs of degradation. It was determined that the pellets contained exactly the same ratios of active ingredient to carrier as was in the starting mixture and it was determined that the growth hormone-releasing hormone had not degraded.

Figure 10:
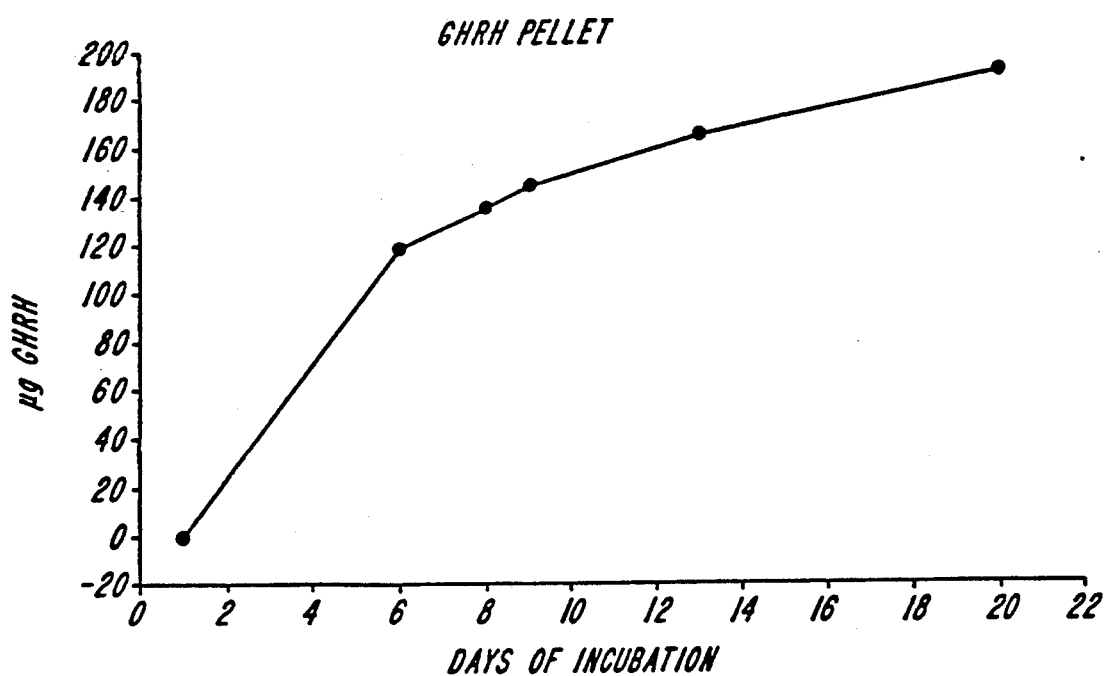
FIG. 10 is a graph showing the cumulative release of drug from a pellet made according to Example 1 plotted against time.

Pellets having a length of 2 mm were placed in in-vitro baths of 1 millileter of physiologic, buffered saline at 25° centrigrade. The amount of GHRH released was measured periodically over a period of 20 days. The pellets were placed in fresh physiological, buffered saline after each measurement After an initial release at a slightly elevated level, the pellets released growth hormone-releasing hormone at an average of approximately 5.7 micrograms per millimeter of pellet per day (days 6-20). The results are shown in FIG. 10.

EXAMPLE 2

Same as example 1 except that the ratio of peptide of lipid is 50 to 50% by weight.

EXAMPLE 3

Same as example 1 except that the ratio of peptide to lipid is 60 to 40% by weight.

Only a particular lipid carrier, cholesterol acetate, has been described in the examples. Other carriers, of course, are contemplated by the invention. For example, pure cholesterol or cholesterol derivatives including cholesteric esters such as cholesterol chloride may be substituted for cholesterol acetate. Furthermore, sterol carriers other than cholesterol or bioerodable carriers with properties substantially equivalent to cholesterol and cholesterol derivatives in terms of size, lipophilicity, crystallinity and melting point may be substituted. Other carriers that may be substituted also include certain fatty acids and neutral fats as described above. While the steroidal carrier described in the example is essentially non-bioactive, bioactive steroidal carriers may be substituted or added and the formed pellet, thus, would deliver two bioactive molecules. The bioactivity of the steroid, of course, may limit its usefulness as a carrier. Steroids include, but by no means are limited to, aldosterone, androstane, androstene, androstenedione, androsterone, cholecalciferol, cholestane, cholic acid, corticosterone, cortisol, cortisol acetate, cortisone, cortisone acetate, deoxycorticosterone, digitoxigenin, ergocalciferol, ergosterol, estradiol, 17-α, estradiol-17β, estriol, estrane, estrone, hydrocortisone, lanosterol, lithocholic acid, mestranol, β-methasone, norethindrone, piednisolone, pregnane, pregnenolone, progesterone, spironolactone, testosterone, triamcinolone and their derivatives.

Likewise, only a particular active ingredient, growth hormone-releasing hormone, has been described in the examples. However, virtually any bioactive peptide having a higher melting point than the carrier may be substituted for growth hormone-releasing hormone. Moreover, more than one peptide may be combined to yield a pellet capable of delivering two peptides having differing bioactivity. For example, luteinizing hormone and follicle stimulating hormone may be combined advantageously. Also, small glycoproteins may be substituted or added as an active ingredient.

Other constituents may be added to the pellet to advantageously affect the properties of the pellet. For example, adding or substituting substances that are less water soluble than cholesterol will cause the pellet to erode more slowly and release drug over a longer period of time. Likewise, erosion of the pellet may be quickened by substituting or adding a substance having a higher water solubility than cholesterol, such as ethyl stearate, stearic acid or fatty acids in their mono-, di- and tri-glyceride forms, as well as alcohol esters. Also, emulsifiers (such as lecithin) and antioxidants (such as Vitamin A) may be added for specific applications.

The apparatus and method for forming a partial melt to produce a partially-fused pellet containing a peptide may be adapted for bioactive molecules other than peptides. It is only necessary that the bioactive molecule have a lower melting temperature than the lipid carrier and that the bioactive molecule retain its bioactive properties under the conditions of forming the partial melt.

It should be understood that various changes and modifications of the embodiments described may be made within the scope of this invention. For example, a pellet having a particular size and shape has been described. Obviously, other sizes and various shapes are contemplated by the invention. Also, while the term nonpolymer has been used to describe the carrier, it was selected in part to distinguish the carrier according to the invention from the macromolecular polymer carriers of the prior art. Thus, it is believed that very small polymers such as a dimer of a steroid may function equivalently to the "nonpolymer" carriers described above. It is intended that all matter contained in the above-description and shown in the accompanying drawings shall be interpreted in an illustrative and not limiting sense.

What is claimed is:

1. A pellet capable of sustained release of a peptide when implanted in the body comprising a peptide drug homogeneously bound in a matrix of a melted and recrystallized, nonpolymer carrier, said peptide drug having a higher melting temperature than said nonpolymer carrier and said nonpolymer carrier being bioerodible, highly crystalline and lipophilic.

2. A pellet as claimed in claim 1 wherein the carrier is a steroid or a steroid derivative.

3. A pellet as claimed in claim 2 wherein the carrier is cholesterol of a cholesterol derivative.

4. A pellet as claimed in claim 1 wherein the carrier is selected from the group consisting of cholesterol, cholesterol acetate and cholesterol chloride.

5. A pellet as claimed in claim 1 wherein the carrier includes a steroid selected from the group consisting of aldosterone, androstane, androstene, androstenedione, androsterone, cholecalciferol, cholestane, cholic acid, corticosterone, cortisol, cortisol acetate, cortisone, cortisone acetate, deoxycorticosterone, digitoxigenin, ergocalciferol, ergosterol, estradiol, 17-α, estradiol 17β, estriol, estrane, estrone, hydrocortisone, lanosterol, lithocholic acid, mestranol, β-methasone, norethindrone, piednisolone, pregnane, pregnenolone, progesterone, spironolactone, testosterone, triamcinolone and their derivatives.

6. A pellet as claimed in claim 2 wherein the peptide is selected from the group consisting of growth hormone and growth hormone-releasing hormone, gonadotropin releasing hormone, and its agonist and antagonist analogues, somatostatin and its analogues, gonadotropins such as luteinizing hormone and follicle stimulating hormone, peptide-T, thyrocalcitonin, parathyroid hormone, glucagon, vasopressin, oxytocin, alpha and beta melanocyte stimulating hormones, peptide molecules which stimulate erythrocyte, leucocyte and immunocyte growth and function such as colony stimulating factors (CFS 1 and 2), erythropoietin and lymphokines (including interleukin I and II), angiotensin I and II, bradykinin, kallidin, adrenocorticotropic hormone, thyroid stimulating hormone, insulin, glucagon and the numerous analogues and congeners of the foregoing peptides.

7. A pellet as claimed in claim 3 wherein the peptide is selected from the group consisting of growth hormone factors, growth hormone and growth hormone-releasing hormone gonadotropin-releasing hormone, and its agonist and antagonist analogues, somatostatin and its analogues, gonadotropins such as luteinizing hormone and follicle-stimulating hormone, peptide-T, thyrocalcitonin, parathyroid hormone, glucagon, vasopressin, oxytocin, alpha and beta melanocyte-stimulating hormones, peptide molecules which stimulate erythrocyte, leucocyte and immunocyte growth and function such as colony stimulating factors (CFS 1 and 2), erythropoietin and lymphokines (including interleukin I and II), angiotensin I and II, bradykinin, kallidin, adrenocorticotropic hormone, thyroid stimulating hormone, insulin, glucagon and the numerous analogues and congeners of the foregoing peptides.

8. A pellet as claimed in claim 4 wherein the peptide is selected from the group consisting of growth hormone factors, growth hormone and growth hormone-releasing hormone, gonadotropin-releasing hormone, and its agonist and antagonist analogues, somatostatin and its analogues, gonadotropins such as luteinizing hormone and follicle-stimulating hormone, peptide-T, thyrocalcitonin, parathyroid hormone, glucagon, vasopressin, oxytocin, alpha and beta melanocyte stimulating hormones, peptide molecules which stimulate erythrocyte, leucocyte and immunocyte growth and function such as colony stimulating factors (CFS 1 and 2), erythropoietin and lymphokines (including interleukin I and II), angiotensin I and II, bradykinin, kallidin, adrenocorticotropic hormone, thyroid stimulating hormone, insulin, glucagon and the numerous analogues and congeners of the foregoing peptides.

9. A pellet as claimed in claim 5 wherein the peptide is selected from the group consisting of growth hormone factors, growth hormone and growth hormone-releasing hormone, gonadotropin-releasing hormone, and its agonist and antagonist analogues, somatostatin and its analogues, gonadotropins such as luteinizing hormone and follicle-stimulating hormone, peptide T, thyrocalcitonin, parathyroid hormone, glucagon, vasopressin, oxytocin, alpha and beta melanocyte-stimulating hormones, peptide molecules which stimulate erythrocyte, leucocyte and immunocyte growth and function such as colony stimulating factors (CFS 1 and 2), erythropoietin and lymphokines (including interleukin I and II), angiotensin I and II, bradykinin, kallidin, adrenocorticotropic hormone, thyroid stimulating hormone, insulin, glucagon and the numerous analogues and congeners of the foregoing peptides.

10. A pellet as claimed in claim 1 wherein said carrier is cholesterol acetate and said peptide drug is growth hormone-releasing hormone.

11. A method for delivering a peptide to the body comprising, implanting in the body a partially-fused pellet containing a peptide drug bound in a matrix of a melted and recrystallized, non-polymer carrier.

12. A method for delivering a peptide to a body comprising, implanting into the body a pellet of a peptide drug homogeneously bound in a matrix of melted and recrystallized, non-polymer carrier, said peptide drug having a higher melting temperature than said non-polymer carrier and said non-polymer carrier being bioerodible, highly crystalline and lipophilic.

13. A partially-fused pellet capable of sustained release of a peptide when implanted in the body, comprising a substantially non-melted peptide drug homogeneously bound in a matrix of a substantially melted and recrystallized non-polymer carrier, said peptide drug having a higher melting temperature than said non-polymer carrier and said non-polymer carrier being bioerodible, highly crystalline and lipophilic.

* * * * *